United States Patent
Herron et al.

(10) Patent No.: US 7,119,225 B1
(45) Date of Patent: Oct. 10, 2006

(54) GOLD CATALYST FOR SELECTIVE OXIDATION

(75) Inventors: Norman Herron, Newark, DE (US); Stephan Schwarz, Wilmington, DE (US); Joe Douglas Druliner, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 434 days.

(21) Appl. No.: 10/344,448

(22) PCT Filed: Aug. 18, 2000

(86) PCT No.: PCT/US00/22865

§ 371 (c)(1),
(2), (4) Date: Feb. 11, 2003

(87) PCT Pub. No.: WO02/16298

PCT Pub. Date: Feb. 28, 2002

(51) Int. Cl.
*C07C 61/00* (2006.01)

(52) U.S. Cl. .................. 560/400; 562/405; 562/407

(58) Field of Classification Search ............... 562/400, 562/405, 407, 527, 528, 538
See application file for complete search history.

(56) References Cited

U.S. PATENT DOCUMENTS

| | | | |
|---|---|---|---|
| 3,149,166 A | 9/1964 | Poehler et al. | |
| 3,449,413 A | 6/1969 | Hartel et al. | |
| 3,717,674 A | 2/1973 | Blay | |
| 4,154,762 A | 5/1979 | Huang et al. | |
| 4,816,606 A | 3/1989 | Brenner et al. | |
| 5,623,090 A * | 4/1997 | Haruta et al. ............... | 568/360 |

OTHER PUBLICATIONS

U.S. Appl. No. 09/245,754 (Druliner, et al.).

* cited by examiner

*Primary Examiner*—Cecilia J. Tsang
*Assistant Examiner*—Hector M. Reyes

(57) ABSTRACT

A supported gold catalyst is used for selective oxidation. In particular, an alcohol or ketone is oxidized to produce the corresponding carboxylic acid, an alcohol is oxidized to produce the corresponding ketone, and xylene is oxidized to produce the corresponding mono-alcohol or di-alcohol.

36 Claims, No Drawings

GOLD CATALYST FOR SELECTIVE OXIDATION

FIELD OF INVENTION

The invention generally relates to an improved catalytic process for selective oxidation utilizing a supported gold catalyst. In particular, the invention generally relates to the oxidation of an alcohol or ketone to produce the corresponding carboxylic acid, an alcohol to produce the corresponding ketone, and xylene to produce the corresponding mono-alcohol or di-alcohol.

BACKGROUND

Gold has not seen much use as a catalyst due to its relative unreactivity. Although limited, several examples of reactions catalyzed by gold have been disclosed. U.S. Pat. No. 3,449,413 describes a method for the preparation of carboxylic acid salts using an alkaline aqueous medium and a copper oxide/gold mixture. U.S. Pat. Nos. 4,154,762, 4,816,606, and U.S. Pat. No. 3,149,166 all use a gold catalyst for the oxidation of a alcohol to form the corresponding ketone, but all perform the reaction at high temperatures and in the gas phase. U.S. Pat. No. 5,623,090 oxidized hydrocarbon to form an alcohol or ketone at lower temperatures and in liquid phase, but added hydrogen gas is required. U.S. Pat. No. 3,717674 states a gold catalyst may be used for the purification of a terephthalic acid reaction mixture via non-specific oxidation of the by-products therein, but no examples are given.

U.S. Ser. No. 09/245,754 (Druliner, et. al) discloses the use of an improved catalytic process for oxidizing cycloalkanes to form a mixture containing the corresponding alcohol and ketone using a heterogeneous gold catalyst.

The present invention describes methods of utilizing a heterogeneous gold catalyst under mild conditions for the preparation of carboxylic acids, ketones, and diacids. These compounds are useful as synthetic intermediates and in a variety of industries, such as polymer production.

SUMMARY OF THE INVENTION

The present invention includes a process for the oxidation of an alcohol or ketone to produce the corresponding carboxylic acid, comprising contacting the alcohol or ketone with a catalytic amount of a heterogeneous catalyst consisting essentially of gold, wherein the reaction is performed in the liquid phase. Preferably the alcohol or ketone is of the formula

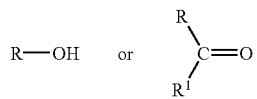

wherein R and R$^1$ are an optionally substituted C$_1$–C$_{20}$ alkane or aromatic compound; most preferred is where the alcohol and ketone are of the formula R—OH or R=O

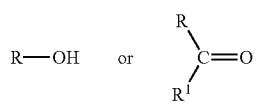

wherein R and R$^1$ are C$_6$–C$_{12}$ alkane, either linear or cyclic, optionally substituted with alkyl or carboxylic acid groups. Optionally, the heterogeneous catalyst is supported on a catalyst support member. A preferred catalyst is Au with about 0.1 percent by weight Pd supported on alumina. The process can also optionally be run in the presence of added oxidant.

The present invention also includes a process for the selective oxidation of xylene to the corresponding mono-alcohol or di-alcohol comprising contacting the xylene with an catalytic amount of a heterogeneous catalyst comprising gold, wherein the reaction is performed in the liquid phase. Optionally, the heterogeneous catalyst is supported on a catalyst support member. A preferred catalyst is Au supported on titania. The process can also optionally be run in the presence of added oxidant.

A process for the oxidation of an alcohol to produce the corresponding ketone comprising contacting the alcohol with a catalytic amount of a heterogeneous catalyst comprising gold, wherein the reaction is performed in the liquid phase. Preferably the alcohol is of the R—CH(OH)—R' wherein R and R' are an optionally substituted C$_1$–C$_{20}$ alkyl or aromatic group; most preferred is where R and R' are an C$_6$–C$_{12}$ alkyl group, either linear or cyclic, optionally substituted with alkyl or carboxylic acid groups. Optionally, the heterogeneous catalyst is supported on a catalyst support member. A preferred catalyst is Au with about 0.1 percent by weight Pd supported on alumina. The process can also optionally be run in the presence of added oxidant.

DETAILED DESCRIPTION OF THE INVENTION

One aspect of the present invention is a method for the oxidation of an alcohol or ketone to produce the corresponding carboxylic acid in the presence of a catalytic amount of a heterogeneous catalyst comprising gold. Another aspect of the invention is a method for the oxidation of an alcohol to produce the corresponding ketone in the presence of a catalytic amount of a heterogeneous catalyst comprising gold. A third aspect of the present invention is a method for the selective oxidation of xylene to the corresponding mono-alcohol or di-alcohol in the presence of a catalytic amount of a heterogeneous catalyst comprising gold.

Advantages of the present heterogeneous catalytic processes, relative to processes employing homogenous metal catalysts, such as metal salts or metal/ligand mixtures, include mild conditions, selectivity to desired products, longer catalyst life, improved yields of useful products, and the absence of soluble metal compounds.

The processes have the advantage over known processes in that they will run in the liquid phase under mild conditions. The conversion rate can vary from little conversion to very high by adjusting the conditions appropriately, as known to anyone skilled in the art. The rate of reaction and selectivity can vary greatly by adjusting the support, oxidant, temperature and time as known to anyone skilled in the art.

The heterogeneous catalysts of the invention include Au, preferably applied to suitable solid supports. The Au is essentially in the form of elemental gold, although some compounds or salts may also be present. The inventive process may also be performed using Au in the presence of other metals, preferably metals of Periodic Group VIII, more preferably Pd. The metal to support percentage can vary from about 0.01 to about 50 percent by weight, and is preferably about 0.1 to about 10 wt. percent. Suitable, presently preferred supports include SiO$_2$ (silica), Al$_2$O$_3$ (alumina), C (carbon), TiO$_2$ (titania), MgO (magnesia) or ZrO$_2$ (zirconia). Alumina and titania are particularly preferred supports, and Au and Au/Pd supported on alumina are particularly preferred catalysts of the invention.

Some of the heterogeneous catalysts of the invention can be obtained already prepared from manufacturers, or they can be prepared from suitable starting materials using methods known in the art. These methods can include sol-gel techniques as described in more detail below. Supported gold catalysts can be prepared by any standard procedure known to give well-dispersed gold, such as evaporative techniques or coatings from colloidal dispersions.

In particular, ultra-fine particle sized gold is preferred. Such small particulate gold (often smaller than 10 nm) can be prepared according to Haruta, M., "Size-and Support-Dependency in the Catalysis of Gold", Catalysis Today 36 (1997) 153–166 and Tsubota et al., Preparation of Catalysts V, pp. 695–704 (1991). Such gold preparations produce samples that are purple-pink in color instead of the typical bronze color associated with gold and result in highly dispersed gold catalysts when placed on a suitable support member. These highly dispersed gold particles typically are from about 3 nm to about 25 nm in diameter.

The catalyst solid support, including SiO$_2$, Al$_2$O$_3$, carbon, MgO, zirconia, or TiO$_2$, can be amorphous or crystalline, or a mixture of amorphous and crystalline forms. Selection of an optimal average particle size for the catalyst supports will depend upon such process parameters as reactor residence time and desired reactor flow rates. Generally, the average particle size selected will vary from about 0.005 mm to about 5 mm. Catalysts having a surface area larger than 10 m$^2$/g are preferred since increased surface area of the catalyst has a direct correlation with increased decomposition rates in batch experiments. Supports having much larger surface areas can also be employed, but inherent brittleness of high-surface area catalysts, and attendant problems in maintaining an acceptable particle size distribution, will establish a practical upper limit upon catalyst support surface area.

The catalysts of the present invention may optionally be silanized by an organosilicon reagent. This treatment prevents fouling of the catalyst, which reduces the catalyst lifetime, by water and organic impurities from the oxidation reactions.

Silanized is defined herein to refer to treatment of the catalyst with either at least one silane, or a mixture of at least one silane and at least one polysiloxane (collectively referred to herein as organosilicon compounds).

Suitable silanes have the formula $R_xSi(R')_{4-x}$ wherein R is a nonhydrolyzable aliphatic, cycloaliphatic or aromatic group having at least 8 to about 20 carbon atoms;

R' is a hydrolyzable group such as but not limited to alkoxy, halogen, acyloxy, acetoxy, hydroxy or mixtures thereof; and x=1 to 3.

For example, silanes useful in carrying out the invention include octyltriethoxysilane, nonyltriethoxysilane, decyltriethoxysilane, dodecyltri-ethoxysilane, tridecyltriethoxysilane, tetradecyltriethoxysilane, pentadecyl-triethoxysilane, hexadecyltrietboxysilane, heptadecyltriethoxysilane and octadecyltriethoxysilane. Preferred examples of silanes include R=8–10 carbon atoms; R'=chloro, ethoxy, methoxy, hydroxy or mixtures thereof; and x=1 to 3. Most preferred silanes are R=8 carbon atoms; R'=ethoxy, and x=3. Mixtures of silanes are contemplated equivalents. Weight content of the silane, based on total silanized catalyst is typically about 0.1 to about 3 weight %, preferably about 0.2 to about 2 weight %.

In an alternative embodiment, a mixture of at least one silane with at least one polysiloxane is useful in carrying out the invention. Suitable polysiloxanes have the formula:

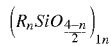

wherein R is organic or inorganic groups; n=0–3; and m$\leq$2. For example, polydimethylsiloxane (PDMS), vinyl phenylmethyl terminated dimethyl siloxanes, divinylmethyl terminated polydimethyl siloxane and the like are suitable polysiloxanes. PDMS is a preferred polysiloxane. The silane useful in the mixture may be the silane described above with R=8–20 carbon atoms, R'=alkoxy and x=1 preferred. Weight content of the silane and polysiloxane, is about 0.1 to about 5.0 weight %, preferably from about 0.2 to 3 weight %. The ratio of silane to polysiloxane can be 1 silane: 2 polysiloxane up to 2 silane: 1 polysiloxane.

The silanes and polysiloxanes are commercially available or can be prepared by processes known in the art such as those described in "Organosilicon Compounds", S. Pawlenko, et al., New York (1980). The method of addition is not especially critical and the catalyst may be treated with the silane in a number of ways. For example, the silane addition can be made neat or prehydrolyzed to a dry base, from a slurry, a filtration step, during drying or at a size operation such as a fluid energy mill, e.g., micronizer, or media mill as described in greater detail in Niedenzu, et al, U.S. Pat. No. 5,501,732, or post blending after micronizing. The polysiloxane addition can be made in conjunction with the silane or post addition to the silanized pigment.

An alternate embodiment that is contemplated is the use of other members of Periodic Groups IV and V in place of Si, such as Ge, P, and As. The catalysts of the invention would thereby be treated with compounds that are the equivalent of the silanes of the instant invention, such as $R_xGe(R')_{4-x}$, $R_xP(R')_{3-x}$, etc.

A "sol-gel technique" is a process wherein a free flowing fluid solution, "sol", is first prepared by dissolving suitable precursor materials such as colloids, alkoxides or metal salts in a solvent. The "sol" is then dosed with a reagent to initiate reactive polymerization of the precursor. A typical example is tetraethoxyorthosilicate (TEOS) dissolved in ethanol. Water, with trace acid or base as catalyst to initiate hydrolysis, is added. As polymerization and crosslinking proceeds, the free flowing "sol" increases in viscosity and can eventually set to a rigid "gel". The "gel" consists of a crosslinked network of the desired material that encapsulates the original solvent within its open porous structure. The "gel" may then be dried, typically by either simple heating in a flow of dry air to produce a xerogel or the entrapped solvent may be removed by displacement with a supercritical fluid such as liquid CO$_2$ to produce an aerogel. These aerogels and xerogels may be optionally calcined at elevated temperatures (>200° C.) which results in products which typically have very porous structures and concomitantly high surface areas.

In practice of the invention, the catalysts can be contacted with the reagents by formulation into a catalyst bed, which is arranged to provide intimate contact between catalysts and reactants. Alternatively, catalysts can be slurried with reaction mixtures using techniques known in the art. The processes of the invention are suitable for batch or for continuous processes. These processes can be performed under a wide variety of conditions.

Suitable reaction temperatures for the processes of the invention will vary depending on the particular reaction employed but will generally range from about 25° C. to about 250° C. Temperatures from about 50° C. to about 180° C. are typically preferred. Reaction pressures also will vary depending on the particular reaction employed but can preferably range from about 69 kPa to about 6900 kPa (10–1000 psi) pressure, and pressures from about 276 kPa to about 4140 kPa (40–600 psi) are more preferred. Reaction time varies in inverse relation to reaction temperature, and typically ranges from about 2 to about 30 minutes.

The processes can be run with a variety of added oxidants such as but not limited to air, oxygen, hypochlorites such as sodium hypochlorite, peroxides such as hydrogen peroxide, iodosobenzene, and hydroperoxides such as t-butyl hydroperoxide or cyclohexylhydroperoxide.

In the method for the oxidation of an alcohol or ketone to produce the corresponding carboxylic acid, the alcohol and ketone are of the formula R—OH or R═O, wherein R is a optionally substituted C1–C20 alkane or aromatic compound. More preferably, R is a C6–C12 alkane, either linear or cyclic, optionally substituted with alkyl or carboxylic acid groups. Preferred reactions include:

6-hydroxycaproic acid→adipic acid
n-decanol→n-decanoic acid
cyclododecanone→dodecandioic acid
cyclohexanone→hexadioic acid
cyclohexanol→hexanoic acid This process has the advantage over known processes in that the reaction will run in the liquid phase under mild conditions.

If the starting alcohol or ketone is cyclic, it is possible to make the corresponding diacid:

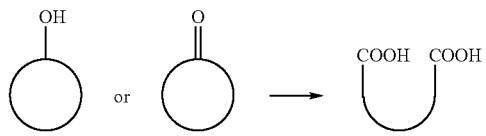

The process is also versatile and can be stopped at any step in the reaction to produce a desired compound, such as but not limited to the alcohol-acid compound:

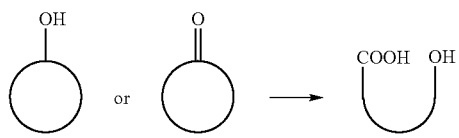

In the method for the oxidation of an alcohol to produce the corresponding ketone, the alcohol is a secondary alcohol of the formula R—CH(OH)—R' wherein R and R' are C1–C20 optionally substituted alkyl groups. More preferably, R and R' are C6–C12 alkyl groups, either linear or cyclic, optionally substituted with alkyl or carboxylic acid groups. Preferred reactions include cyclohexanol→cyclohexanone.

In the method for the selective oxidation of xylene to the corresponding mono-alcohol or di-alcohol, the xylene can be any of or a mixture of the para, meta, and ortho isomers. The preferred isomer is para. The reaction proceeds in the order xylene→alcohols→acids, and can be stopped at any point in the sequence to produce the desired product.

Other alkyl aromatics can also be used in the instant process, including but not limited to cumene, toluene, durene, mesitylene, and alkyl-substituted naphthalenes.

The following definitions are used herein and should be referred to for claim interpretation.

| A | cyclohexanol |
| BSTFA | bis(trimethylsilyl)trifluoroacetamide |
| CB | chlorobenzene |
| CHHP | cyclohexylhydroperoxide |
| HyCap | 6-hydroxycaproic acid, $CH_2OH(CH_2)_4COOH$ |
| K | cyclohexanone |

The following non-limiting Examples are meant to illustrate the invention but are not intended to limit it in any way.

EXAMPLES

GC analyses of reaction products were done either directly on reaction product solutions, or following derivatization using BSTFA (bis(trimethyl-silyl) trifluoroacetamide)/1% trimethylchlorosilane, Supelco, Inc., Bellefornte, Pa.), a standard derivatizing agent for GC analyses. GC analyses were done using a 15 m DB-17 capillary column with a 0.32 mm internal diameter (J. & W. Scientific, Folsum, Calif.).

All calculations of conversion of starting compounds to products are based on molarities of products as determined by GC. The molarity (M) of a given product compound was calculated from the equation:

$$M_{Compound} = \frac{area\%_{Compound} \times M_{CB} \times R.F._{Compound}}{area\%_{CB}}$$

$R.F._{Compound}$ (GC response factor for a given compound) was determined from calibration solutions containing known amounts of each product compound measured by GC and CB from the equation:

$$R.F._{Compound} = \frac{M_{Compound} / area\%_{Compound}}{M_{CB} / area\%_{CB}}$$

In Examples containing no internal GC standard, Conversions were determined from ratios of product compounds/(product compounds+starting compound).

Examples 1–6 involve the use of CHHP and tBu-OOH (tert-butylhydro-peroxide) in combination with heterogeneous 1% Au+0.1%Pd/α-Al$_2$O$_3$ to carry out the oxidation of various organic compounds. Examples 7–11 involve the use of air, in combination with heterogeneous 1% Au+0.1%Pd/α-Al$_2$O$_3$ to carry out the oxidation of various organic compounds. Examples 12 and 14 were done using heterogeneous 1% Au α-Al$_2$O$_3$. These catalysts were prepared by Englehard Corp., 12 Thompson Rd., E. Windsor, Conn. for E. I. du Pont de Nemours and Company, using a proprietary procedure based on the general procedure shown in Experiment 1 below, with the addition of palladium tetraamine chloride along with the gold chloride.

Example 13 was done using heterogeneous 1% Au α-Al$_2$O$_3$ and 1% Au α-TiO$_2$. All catalysts were prepared using the general procedures shown below.

EXPERIMENT 1

10 g of titania was slurried into a solution of 0.2 g gold chloride in 25 mL water and 1 drop HCl added. After stirring for 10 mins, the pH was adjusted to 9.6 with sodium carbonate solution (1 M). Stirring was continued for 10 more minutes then 0.69 g sodium citrate was added and the slurry gently agitated for a further 2 hrs. The gray solid was filtered off and washed well with water, suction dried and then calcined in flowing air at 250° C. for 5 hrs. The recovered purple solid was collected and used for catalysis as described below.

10 g of α-alumina were slurried into a solution of 0.2 g gold chloride in 25 mL water and 1 drop HCl added. After stirring for 10 min., the pH was adjusted to 9.6 with sodium carbonate solution (1 M). Stirring was continued for 10 more minutes then 0.69 g sodium citrate was added and the slurry gently agitated for a further 2 hrs. The gray solid was filtered off and washed well with water, suction dried and then calcined in flowing air at 250° C. for 5 hrs. The recovered purple solid was collected and used for catalysis as described below.

EXAMPLE 1

Into a ~1 mL GC vial was placed a Teflon®-coated stir bar, 0.0139 g catalyst, 0.0168 g (0.127 mmole) 6-hydroxycaproic acid (HyCap) and 0.3 mL undecane. The vial was sealed using a septum cap and was placed in a heated aluminum block heater. The contents of the vial were stirred at 150° C. for 5 minutes. Next, 0.030 mL of CHHP/CB (chlorobenzene GC internal standard) was added by syringe. The CHHP/CB solution consisted of ~37.9% CHHP, ~9.6% CB, with the balance comprised of K and A. The amount of CHHP added was ~0.0114 g (~0.098 mmole). After 5 minutes, the vial was removed from the block heater and was immersed in wet ice. 1.2 mL of undecane was added to the reaction vial, the contents shaken and 0.2 mL of reaction mixture was combined with 1 mL of BSTFA. The BSTFA sample was stirred and heated at 50° C. for 1 hr, cooled to room temperature and the liquid phase analyzed by GC. The %conversion of CHHP to products was 100%. The %conversion of HyCap to adipic acid was 26%.

EXAMPLE 2

Into a ~1 mL GC vial was placed a Teflon®-coated stir bar, 0.0102 g catalyst, 0.0202 g (0.153 mmole) 6-hydroxycaproic acid (HyCap) and 0.3 mL undecane. The vial was sealed using a septum cap and was placed in a heated aluminum block heater. The contents of the vial were stirred at 150° C. for 5 minutes. Next, 0.060 mL of tBu-OOH/CB was added by syringe. The amount of tBu-OOH added was ~0.0135 g (~0.15 mmole). After 5 minutes, the vial was removed from the block heater and was immersed in wet ice. 1.2 mL of undecane was added to the reaction vial, the contents shaken and 0.5 mL of reaction mixture was combined with 1 mL of BSTFA. The BSTFA sample was stirred and heated at 50° C. for 1 hr, cooled to room temperature and the liquid phase analyzed by GC. The %conversion of HyCap to adipic acid was 50%.

EXAMPLE 3

Into a ~1 mL GC vial was placed a Teflon®-coated stir bar, 0.0101 g catalyst, supplied by Calsicat, 0.0163 g (0.103 mmole) n-$C_{10}H_{21}OH$ and 0.3 mL undecane. The vial was sealed using a septum cap and was placed in a heated aluminum block heater. The contents of the vial were stirred at 150° C. for 5 minutes. Next, 0.060 mL of tBu-OOH/CB was added by syringe. The amount of tBu-OOH added was ~0.0135 g (~0.15 mmole). After 5 minutes, the vial was removed from the block heater and was immersed in wet ice. 1.2 mL of undecane was added to the reaction vial, the contents shaken and 0.5 mL of reaction mixture was combined with 1 mL of BSTFA. The BSTFA sample was stirred and heated at 50° C. for 1 hr, cooled to room temperature and the liquid phase analyzed by GC. The %conversion of n-$C_{10}H_{21}OH$ to $C_9H_{19}CO_2H$ was 14%.

EXAMPLE 4

Into a ~1 mL GC vial was placed a Teflon®-coated stir bar, 0.0103 g catalyst, supplied by Calsicat, 0.0192 g (0.19 mmole) cyclohexyl alcohol (A) and 0.3 mL undecane. The vial was sealed using a septum cap and was placed in a heated aluminum block heater. The contents of the vial were stirred at 150° C. for 5 minutes. Next, 0.060 mL of tBu-OOH/CB was added by syringe. The amount of tBu-OOH added was ~0.0135 g (~0.15 mmole). After 5 minutes, the vial was removed from the block heater and was immersed in wet ice. 1.2 mL of undecane was added to the reaction vial, the contents shaken and 0.5 mL of reaction mixture was combined with 1 mL of BSTFA. The BSTFA sample was stirred and heated at 50° C. for 1 hr, cooled to room temperature and the liquid phase analyzed by GC. The %conversion of A to K (cyclohexanone) was 39%.

EXAMPLE 5

Into a ~1 mL GC vial was placed a Teflon®-coated stir bar, 0.0101 g catalyst, supplied by Calsicat, 0.0498 g (0.377 mmole) HyCap and 0.3 mL undecane. The vial was sealed using a septum cap containing a single hole in it and it was placed in a stainless steel block heater fitted with an o-ring seal and a valve for admitting reaction gases. The block heater was pressurized to 500 psi with air. The contents of the vial were stirred and heated to 170° C. (42 minutes heatup time) and held at 170° C. for 30 minutes. The reactor was removed from the heating element and was immersed in wet ice. GC analysis of the final reaction product was done on a sample prepared using 1 mL of BSTFA added to the reaction mixture, stirred at 50° C. for 1 hr. The %conversion of HyCap to adipic acid was 30%.

EXAMPLE 6

Into a ~1 mL GC vial was placed a Teflon®-coated stir bar, 0.0104 g catalyst, 0.0104 g (0.078 mmole) HyCap and 1.0 mL cyclohexane. The vial was sealed using a septum cap containing a single hole in it and it was placed in a stainless steel block heater fitted with an o-ring seal and a valve for admitting reaction gases. The block heater was pressurized to 500 psi with air. The contents of the vial were stirred and heated to 160° C. (40 minutes heatup time) and held at 160° C. for 20 minutes. The reactor was removed from the heating element and was immersed in wet ice. GC analysis of the final reaction product was done on a sample prepared using 1 mL of BSTFA added to the reaction mixture, stirred at 50° C. for 1 hr. The %conversion of HyCap to adipic acid was 60%. HyCap was also converted to caprolactone (8%) and to a dimer of HyCap (21%). Cyclohexane was converted to K (~1.2%), A (~4.0%), CHHP (~0.12%) and to 2-cyclohexenone (~0.06%).

EXAMPLE 7

Into a ~1 mL GC vial was placed a Teflon®-coated stir bar, 0.0104 g, 0.0111 g (0.084 mmole) HyCap and 0.5 mL $H_2O$. The vial was sealed using a septum cap containing a single hole in it and it was placed in a stainless steel block heater fitted with an o-ring seal and a valve for admitting reaction gases. The block heater was pressurized to 500 psi with air. The contents of the vial were stirred and heated to 160° C. (40 minutes heatup time) and held at 160° C. for 20 minutes. The reactor was removed from the heating element and was immersed in wet ice. GC analysis of the final reaction product was done on a sample prepared by first evaporating the reaction mixture to dryness at ~100° C. and with an $N_2$ purge. Next, 1 mL of BSTFA was added to the reaction solids and was stirred at 50° C. for 1 hr. The %conversion of HyCap to adipic acid was 97%.

EXAMPLE 8

Into a ~1 mL GC vial was placed a Teflon®-coated stir bar, 0.0100 g catalyst, 0.102 g (0.0.56 mmole) cyclododecanone and 0.5 g cyclododecane. The vial was sealed using a septum cap containing a single hole in it and it was placed in a stainless steel block heater fitted with an o-ring seal and a valve for admitting reaction gases. The block heater was pressurized to 500 psi with air. The contents of the vial were stirred and heated to 170° C. (42 minutes heatup time) and held at 170° C. for 30 minutes. The reactor was removed from the heating element and was immersed in wet ice. GC analysis of the final reaction product, treated with BSTFA and stirred at 50° C. for 1 hr gave a %conversion of cyclododecanone to dodecandioic acid of ~2%.

EXAMPLE 9

Into a ~1 mL GC vial was placed a Teflon®-coated stir bar, 0.0103 g catalyst, 0.102 g (0.0.56 mmole) cyclododecanone and 0.5 g $H_2O$. The vial was sealed using a septum cap containing a single hole in it and it was placed in a stainless steel block heater fitted with an o-ring seal and a valve for admitting reaction gases. The block heater was pressurized to 500 psi with air. The contents of the vial were stirred and heated to 170° C. (42 minutes heatup time) and held at 170° C. for 30 minutes. The reactor was removed from the heating element and was immersed in wet ice. GC analysis of the final reaction product was done on a sample prepared by first evaporating the reaction mixture to dryness at ~100° C. and with an $N_2$ purge. Next, 1 mL of BSTFA was added to the reaction solids and was stirred at 50° C. for 1 hr. The %conversion of cyclododecanone to dodecandioic acid was ~6%.

EXAMPLE 10

Into a ~1 mL GC vial was placed a Teflon®-coated stir bar, 0.0101 g catalyst, 0.0210 g (0.159 mmole) Hycap and 0.5 mL $H_2O$. The vial was sealed using a septum cap containing a single hole in it and it was placed in a stainless steel block heater fitted with an o-ring seal and a valve for admitting reaction gases. The block heater was pressurized to 500 psi with air. The contents of the vial were stirred and heated to 160° C. (53 minutes heatup time) and held at 160° C. for 20 minutes. The reactor was removed from the heating element and was immersed in wet ice. GC analysis of the final reaction product was done on a sample prepared by combining ~30 μl of product solution with ~1.5 mL of BSTFA, and the mixture was stirred at 50° C. for 1 hr. The %conversion of HyCap to adipic acid was 42%.

COMPARATIVE EXAMPLE 10A

Into a ~1 mL GC vial was placed a Teflon®-coated stir bar, 0.0100 g catalyst [10% Co on silica], 0.0206 g (0.156 mmole) HyCap and 0.5 mL $H_2O$. The vial was sealed using a septum cap containing a single hole in it and it was placed in a stainless steel block heater fitted with an o-ring seal and a valve for admitting reaction gases. The block heater was pressurized to 500 psi with air. The contents of the vial were stirred and heated to 160° C. (53 minutes heatup time) and held at 160° C. for 20 minutes. The reactor was removed from the heating element and was immersed in wet ice. GC analysis of the final reaction product was done on a sample prepared by combining ~30 μl of product solution with ~1.5 mL of BSTFA, and the mixture was stirred at 50° C. for 1 hr. The %conversion of HyCap to adipic acid was ~0%.

EXAMPLE 11

Into a ~1 mL GC vial was placed a Teflon®-coated stir bar, 0.0103 g catalyst [1% Au on alphaAl$_2$O$_3$], supplied by Engelhard, 0.0206 g (0.156 mmole) 6-hydroxycaproic acid (HyCap) and 0.5 mL 0.65 M aqueous NaOCl [Clorox solution]. The vial was sealed using a septum cap and was placed in a heated aluminum block heater. The contents of the vial were stirred at 90° C. for 10 minutes. ~30 μL of product solution was combined with 1 mL of BSTFA, and the mixture was stirred at 50° C. for 1 hr. The sample was analyzed by GC. The %conversion of HyCap to adipic acid was ~24%.

EXAMPLE 12

Into a ~1 mL GC vial was placed a Teflon®-coated stir bar, 0.0105 g catalyst, 0.0100 g (0.076 mmole) 6-hydroxycaproic acid (HyCap), 0.0402 g (0.183 m mole) iodosobenzene and 0.5 mL cyclohexane. The vial was sealed using a septum cap and was placed in a heated aluminum block heater. The block heater was pressurized to 500 psi with $N_2$ and the contents of the vial were stirred at 90° C. for 10 minutes. The contents of the vial were combined with 1 mL of BSTFA and the mixture was stirred at 50° C. for 1 hr. The sample was analyzed by GC. The %conversion of HyCap to adipic acid was ~17%.

EXAMPLE 13

5 mL of a stock solution containing 90% p-xylene and 10% acetic acid with 0.1% o-dichlorobenzene are placed in a shaker tube. 500 mg of catalyst are added and the tube loaded into a rack. The rack was pressured to 500 psi air and heated to 150° C. for 5 hrs while shaking vigorously. After cooling the sample was recovered and 5 mL pyridine added. 4–5 Pellets dry 4A molecular sieves were used to dry the sample and then 0.5 mL BSTFA was added to a 1 mL portion of the solution. After stirring for 10 mins the sample was analyzed by GC on a capillary column. Results are shown in Table 1 below.

TABLE 1

| Catalyst | % Conversion | % 4-methyl-benzaldehyde | % 4-methyl-benzylalcohol | % toluic acid | % 1,4 benzene-dimethanol | % 1,2 di-(4-methylphenyl)-ethane | % terephthalic acid |
|---|---|---|---|---|---|---|---|
| None | 24.5 | 18 | 13 | 66 | 0 | 0.4 | 2.4 |
| 1% Au on | 36.2 | 4 | 71 | 9 | 15 | 0.0 | 0.0 |

TABLE 1-continued

| Catalyst | % Conversion | % 4-methyl-benzaldehyde | % 4-methyl-benzylalcohol | % toluic acid | % 1,4 benzene-dimethanol | % 1,2 di-(4-methylphenyl)-ethane | % terephthalic acid |
|---|---|---|---|---|---|---|---|
| TiO$_2$ 1% Au on α-alumina | 9.8 | 6 | 69 | 16 | 9 | 0.0 | 0.0 |

There is a marked shift towards alcohol formation relative to simple autoxidation.

EXAMPLE 14

Into a 1 L GC vial was placed a Teflon®-coated stir bar, 0.0204 g catalyst (1%Au on alpha Al$_2$O$_3$) 0.0209 g (0.169 mmole) of 5-hydroxymethylfurfural and 0.5 mL methanol. The vial was sealed using a septum cap containing a single hole in it and was placed in stainless steel block heater fitted with an o-ring seal and a valve for admitting reaction gases. The block heater was pressurized to 500 psi with air. The contents of the vial were stirred and heated to 80° C. (24 minutes heatup time) and held at 80° C. for 2 hr. The reactor was removed from the heating element and was cooled in wet ice. The vial was removed from the reactor, and the methanol removed by purging with a N$_2$ stream at 60° C. for about an hour. GC analysis of the final reaction mixture was done on a sample prepared using 1 mL of BSTFA added to the reaction mixture, stirred at 50° C. for 1 hr. The ratios of final products was approximately 49% 2-hydroxymethyl-5-carbomethoxyfuran, 37% 2-hydroxymethyl-5-furancarboxylic acid, 2% 2,5-furan dicarboxylic acid and 11% unreacted 5-hydroxymethylfurfural.

We claim:

1. A process for the oxidation of a primary alcohol to produce the corresponding carboxylic acid comprising contacting the alcohol with a catalytic amount of a supported heterogeneous catalyst consisting essentially of gold, wherein the catalyst is supported on a support material selected from SiO$_2$, Al$_2$O$_3$, carbon, TiO$_2$, MgO, and zirconia and wherein the reaction is performed in the liquid phase.

2. The process according to claim 1 wherein the alcohol is of the formula

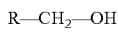
R—CH$_2$—OH wherein R is an optionally substituted C$_1$–C$_{20}$ alkyl or aromatic group.

3. The process according to claim 2 wherein R is a C$_6$–C$_{12}$ alkyl group, either linear or cyclic, optionally substituted with alkyl or carboxyic acid groups.

4. The process according to claim 3 wherein the alcohol is selected from the group consisting of 6-hydroxycaproic acid, n-decanol and 5-hydroxymethylfurfural.

5. The process according to claim 1 wherein the reaction temperature is from about 25° C. to about 200° C.

6. The process according to claim 1 wherein the process is run in the presence of added oxidant.

7. The process according to claim 6 wherein the oxidant is selected from the group consisting of oxygen, iodosobenzene, a hypochlorite and a hydroperoxide.

8. The process according to claim 1 wherein the gold is dispersed on the support material in the form of particles having a diameter from about 3 nm to about 25 nm.

9. The process according to claim 8 wherein the catalyst is about 1.0 percent by weight Au with about 0.1 percent by weight Pd supported on alumina.

10. A process for the oxidation of a ketone to produce the corresponding carboxylic acid comprising contacting the ketone with a catalytic amount of a supported heterogeneous catalyst consisting essentially of gold, wherein the catalyst is supported on a support material selected from SiO$_2$, Al$_2$O$_3$, carbon, TiO$_2$, MgO, and zirconia and wherein the reaction is performed in the liquid phase.

11. The process according to claim 10 wherein the ketone is of the formula

wherein R and R$^1$ are an optionally substituted C$_1$–C$_{20}$ alkyl or aromatic group, and wherein R and R$^1$ can optionally together form a ring.

12. The process according to claim 11 wherein R and R$^1$ are C$_6$–C$_{12}$ alkyl groups, either linear or cyclic, optionally substituted with alkyl or carboxylic acid groups, and wherein R and R$^1$ can optionally together form a ring.

13. The process according to claim 10 wherein the ketone is cyclododecanone.

14. The process according to claim 10 wherein the reaction temperature is from about 25° C. to about 200° C.

15. The process according to claim 10 wherein the process is run in the presence of added oxidant.

16. The process according to claim 15 wherein the oxidant is selected from the group consisting of oxygen, iodosobenzene, a hypochlorite and a hydroperoxide.

17. The process according to claim 10 wherein the gold is dispersed on the support material in the form of particles having a diameter from about 3 nm to about 25 nm.

18. The process according to claim 10 wherein the catalyst is about 1.0 percent by weight Au with about 0.1 percent by weight Pd supported on alumina.

19. The process according to claim 11 wherein R and R$^1$ together form a ring and wherein the carboxylic acid that is produced is the corresponding linear diacid.

20. A process for the oxidation of a secondary alcohol to produce the corresponding ketone comprising contacting the secondary alcohol with a catalytic amount of a supported heterogeneous catalyst consisting essentially of gold, wherein the catalyst is supported on a support material selected from SiO$_2$, Al$_2$O$_3$, carbon, TiO$_2$, MgO, and zirconia and wherein the reaction is performed in the liquid phase.

21. The process according to claim 20 wherein the alcohol is of the formula R—CH(OH)—R' wherein R and R' are an optionally substituted C1–C20 alkyl or aromatic group, and wherein R and R' can optionally together form a ring.

22. The process according to claim 20 wherein R and R' are an C$_6$–C$_{12}$ alkyl group, either linear or cyclic, optionally substituted with alkyl or carboxylic acid groups, and wherein R and R' can optionally together form a ring.

23. The process according to claim 22 wherein the alcohol is cyclohexanol.

24. The process according to claim 20 wherein the reaction temperature is from about 25° C. to about 200° C.

25. The process according to claim 20 wherein the process is run in the presence of added oxidant.

26. The process according to claim 25 wherein the oxidant is selected from the group consisting of oxygen, iodosobenzene, a hypochlorite and a hydroperoxide.

27. The process according to claim 20 wherein the gold is dispersed on the support material in the form of particles having a diameter from about 3 nm to about 26 nm.

28. The process according to claim 27 wherein the catalyst is about 1.0 percent by weight Au with about 0.1 percent by weight Pd supported on alumina.

29. The process according to claim 21 wherein R and $R^1$ together form a ring and wherein the ketone that is produced is further reacted to produce the corresponding linear diacid.

30. A process for the selective oxidation of xylene to the corresponding mono-alcohol or di-alcohol comprising contacting the xylene with an catalytic amount of a supported heterogeneous catalyst consisting essentially of gold, wherein the catalyst is supported on a support material selected from $SiO_2$, $Al_2O_3$, carbon, $TiO_2$, MgO, and zirconia and wherein the reaction is performed in the liquid phase.

31. The process according to claim 30 wherein the reaction temperature is from about 25° C. to about 200° C.

32. The process according to claim 30 wherein the process is run in the presence of added oxidant.

33. The process according to claim 32 wherein the oxidant is selected from the group consisting of oxygen, iodosobenzene, a hypochlorite and a hydroperoxide.

34. The process according to claim 30 wherein the xylene is para-xylene.

35. The process according to claim 30 wherein the gold is dispersed on the support material in the form of particles having a diameter from about 3 nm to about 25 nm.

36. The process according to claim 35 wherein the catalyst is about 1.0 percent by weight Au on titania.

* * * * *